United States Patent [19]

Rolfes

[11] Patent Number: 4,531,515

[45] Date of Patent: Jul. 30, 1985

[54] EXTERIOR ORTHOPEDIC ADJUSTABLE HINGE BRACE

[76] Inventor: Thomas A. Rolfes, 1943 Green Point Dr., Apt. No. 102, Kirkwood, Mo. 63122

[21] Appl. No.: 613,744

[22] Filed: May 23, 1984

Related U.S. Application Data

[63] Continuation of Ser. No. 522,600, Aug. 12, 1983, abandoned, which is a continuation of Ser. No. 472,921, Mar. 7, 1983, Pat. No. 4,481,941.

[51] Int. Cl.³ ............................................. A61F 3/00
[52] U.S. Cl. ................................................ 128/87 R
[58] Field of Search ................ 128/87 R, 89 R, 80 R, 128/80 F, 88, 80 G

[56] References Cited

U.S. PATENT DOCUMENTS

| | | | |
|---|---|---|---|
| 2,753,864 | 7/1956 | Weidemann, Jr. | 128/87 R |
| 3,993,056 | 11/1976 | Rabischong et al. | 128/89 R |
| 4,088,130 | 5/1978 | Applegate | 128/80 F |
| 4,169,467 | 10/1979 | Rabischong et al. | 128/80 G |
| 4,340,041 | 7/1982 | Frank | 128/88 X |
| 4,481,941 | 11/1984 | Rolfes | 128/88 |

FOREIGN PATENT DOCUMENTS

1324883 12/1963 France ............................ 128/80 F

*Primary Examiner*—John D. Yasko
*Assistant Examiner*—Christa K. Scott
*Attorney, Agent, or Firm*—Rogers, Howell, Renner, Moore & Haferkamp

[57] ABSTRACT

An adjustable orthopedic exterior hinge brace has an upper brace extension pivotally connected to a lower brace extension, with structure limiting relative pivoting of the extensions in both directions comprising a limiting member attached at one point of the inner end of one of the extensions so that when the other extension pivots it contacts said limiting member to the restricted in further pivotal movement in a first rotational direction, and a second limiting member mounted at a second point about the inner end of an extension so that when the lower extension pivots in the opposite direction its further pivotal movement is blocked by the second limiting member, with there being structure to allow the positions of the two limiting members to be adjusted to different positions about the extensions so that the degree of arcuate movement of the two extensions relative to each other can be adjusted to a variety of positions depending upon the placement of the limiting members, and in the preferred embodiment an extension has holes in which the limiting members are mounted, with the structure being of universal nature so that it can be applied to either side of a body member by straps or other structures securing it about the body joint, and so that it can be adjusted while mounted to the body in operation.

23 Claims, 12 Drawing Figures

EXTERIOR ORTHOPEDIC ADJUSTABLE HINGE BRACE

This application is a continuation of application Ser. No. 522,600, filed 8/12/83, abandoned; which is a continuation of application Ser. No. 472,921, filed 3/7/83, U.S. Pat. No. 4,481,941.

BACKGROUND OF THE INVENTION

This invention relates to orthopaedic hinged braces for use with human body bone joints by being mounted on the exterior of the skin surface surrounding the joint.

When a patient is being treated for an injury, it is often times desirable to limit the patient's range of bone joint pivoting in the initial stages of healing, so that at first the range of movement is limited, but so that as time passes and as healing progresses, a greater range of movement is allowed to prevent atrophy and to allow a controlled rate of the patient working himself back in condition. Furthermore, in some situations only a limited range of movement may be desired for a previously injured body part.

In the prior art, braces have been used to help support knees. Such braces have an upper and a lower brace extension pivotally connected. Some of these knee braces have had ways to restrict pivotal movement of the restrictions. In one prior art device, this has been by a metal wire with its two ends each secured by a screw nut to points on each of the two extensions, so that the wire tension limits the extension of the knee when the brace is on, but does not limit flexion of the knee. The screws can be loosened to detach the connection of the wire ends to the brace extensions to allow the length of the wire between the two nuts to be shortened or lenghtened to thus increase or decrease the amount of extension permitted. Such a device has a number of drawbacks. For one, the wire can get caught on other objects and trip the user. This is especially a problem when the brace is flexed quite a bit, and the wire is slack and loops out from the brace. Also the fastening points of the wire are away from the pivotal connection of the braces. The wire is subject to breaking under tension, and also is subject to contact from other objects which can gash it and weaken it to thus expedite breaking, or in fact cut the wire. The wire furthermore can limit only flexion.

In another device used on the knee there are top and bottom brace extensions pivotally connected by a screw. In between each of the extension ends where the pivotal connection is located, there is a circular plate with a center hole which has on one side a plurality of V grooves radiating out from its center and on the other side has a lug projecting outwardly therefrom. The inner end of one of the brace extensions likewise has, on one side, V grooves radiating out from the point of pivotal connection of that extension, which grooves mesh with the V grooves of the intermediate plate to lock movement of the plate relative to the brace extension. The other brace extension has on the inside of its inner end four recesses of arcuate shape, each of a different arcuate length, and each of which can receive the lug on the intermediate plate. The two extensions and the intermediate plate are secured by a large screw and nut arrangement, as well as with a sleeve that provides centering of the members. The first extension can thus pivot relative to the second extension with the range of movement dependent upon which of the arcuate recesses within which the lug is placed. In one recess the pivotal range is from 0 degree-70 degrees, in another recess the range is 0 degree-10 degrees, in another 0 degree-40 degrees, and in the fourth position the position of the brace extensions are fixed relative to each other and no pivoting occurs.

This type of device has disadvantage in that to readjust the pivoting range, the brace should be taken off the user, and the pivot screw connecting the members removed to detach the first brace extension from the second extension. The intermediate plate must be disengaged from the extension having the arcuate recesses, and rotated so the lug can be inserted in another selected recess. During all this, the hand must be used to hold the screw and sleeve to prevent them from falling on the floor. After this adjusting has occurred, the other brace extension can again be mounted to the pivot screw and the nut attached to hold the members together. This is an awkward procedure in which the members can fall on the floor and be lost or broken and furthermore takes excessive time even after the brace is detached from the body. The device comprises a number of parts, and it provides only three ranges of actual pivot movement. The fact that the recesses are located in a circular arrangement about the pivot point necessarily limits the possible ranges of pivoting that can be provided.

In the prior art there have also been plastic rods which have been mounted to casts on the body which allow some flexing simply because they were not completely rigid. However, with such flexible plastic brace extensions there is no way to adjust the range of pivotal movement and the range of movement is simply dependent on the degree of rigidity of the rod.

SUMMARY OF THE INVENTION

The present invention improves over the prior art. The control hinge brace of this invention comprises upper and lower, (or first and second) brace extensions pivotally mounted to one another with means for selectively limiting the range of pivoting of the upper extension with respect to the lower extension, which means is capable of adjustment while pivotal connection of the extensions remains fixed, and while the brace is still mounted in use on the body with safety and stability.

In the preferred embodiment, the lower portion of the upper extension has a plurality of arranged holes about the hinge pin, and at least one limiting member such as a pin or screw extending through a hole to block and limit the pivoting motion of the lower brace extension. The limiting pin or screw can be selectively placed to prevent any flexion of the hinge at all, such as is desired, for example, with illustration with a hip brace, during the first three weeks or so after setting of a hip brace for a patient with a fracture of the proximal femur which is nondisplaced. After three weeks or so, the limiting pin or screw can be replaced to another pair of holes to allow flexion over a 15°-20° range. The amount of flexion motion can be adjusted with the progress of healing. Two limiting members can be used to limit rotation in both directions to thus limit the range of flexion and extension of the joint. The limiting members are placed in different holes around the hinge pin so that one of the limiting members blocks and limits pivotal movement of the lower extension in one direction, and the other limiting members blocks and limits pivotal movement of the lower extension in the other direction. The limiting members can be, in the preferred embodiment, screws threaded in conforming threads in the holes.

The lower portion of the upper extension having the holes can be forked in to two ends or plates so that the limiting member, or the two limiting members, can extend in holes in both plates, to thus reinforce the support of the limiting member by providing support on both ends of the member to avoid a cantilever effect. The controlled motion that the hinge brace permits helps to prevent the muscles from atrophying and the joint from deteriorating. The adjustable nature of the hinge brace facilitates providing the range of motion needed for proper healing or prevention of injury.

The adjustable range of motion of the hinge permits, for example in use with the hip, maximum flexion of the joint, that is raising of the knee, and extension, that is lowering of the knee, consistent with the patient's injuries.

The ends of the hinged brace can have means, such as holes, to allow the brace ends to be adjustably mounted to the supporting members with which it is used. In the illustration of the specification, the brace is mounted to a belt around the waist and a thigh support, each of which has a sheath with holes to be aligned with the holes in the brace ends. The hinged brace of the invention can be used for human body joints such as the ankle, knee or elbow, for example.

With the knee, the pins in the holes of the first extension can be placed to prevent hyperextension of the knee such as desired for the healing of the knee and prevention of reinjury of the knee. The pins can also be placed to prevent excessive flexion of the knee. The adjustable hinge thus has application during the healing process of the knee, and also after healing has occurred so as to prevent reinjuring the weakened part of the body, such as by an athlete who participates in his sport after recovering from a knee operation.

The present invention thus provides for adjustable structure to limit the pivotal range of the brace extensions, which is adjustable while the brace is still affixed to the body and while the pivotal connection of the extensions to each other remains secure and operable. There is thus no need go through the cumbersome procedure of removing the brace from the body in which case the user no longer has the benefits of the brace, and further there is no need to waste time disengaging the pivotal connection of the brace extensions to one another.

The adjustment can be made while the brace is still mounted, and in the preferred embodiment in adjusting the pivotal range in one direction it is necessary to detach only one member from the brace, i.e., a limiting member and to reposition it at a different location. If two limiting members are used, and the pivotal range is to be adjusted for both directions, it is necessary to only detach and relocate the two limiting members. The small number of parts used facilitates ease of manufacture and assembly, and minimizes the necessary material for use. It further minimizes the amount of time necessary to make an adjustment and because of the simplicity and elegance of the design there are no awkward processes whereby components can be easily dropped on the floor or lost during readjustment. The structure is of a universal nature to allow the brace to be used on either the right or left limb, with the positioning of the limiting screws being reversed as to controlling the degree of flexion and extension of the body limb.

The variety of range of pivotal movement is great, and is only limited by the number of holes that are selected to be placed about the pivotal connection. The diameter of the holes can be varied to use more holes, with the possibility of using stronger limiting members for small holes, and further the holes can be provided in rings around the pivotal connection.

The limiting members in the preferred embodiment are small and do not project out from the brace where they can snag or engage other objects to thus trip the user, nor are they in a position where they can engage objects which can gash or cut into them to weaken them so that breaking of them is easier. The device can thus limit both flexion and extension in convenient simple, stable and safe fashion, and is an improvement over the state of the art.

DESCRIPTION OF THE PREFERRED EMBODIMENT

Figures 1, 2, 3, 4, 5, 6, 7:
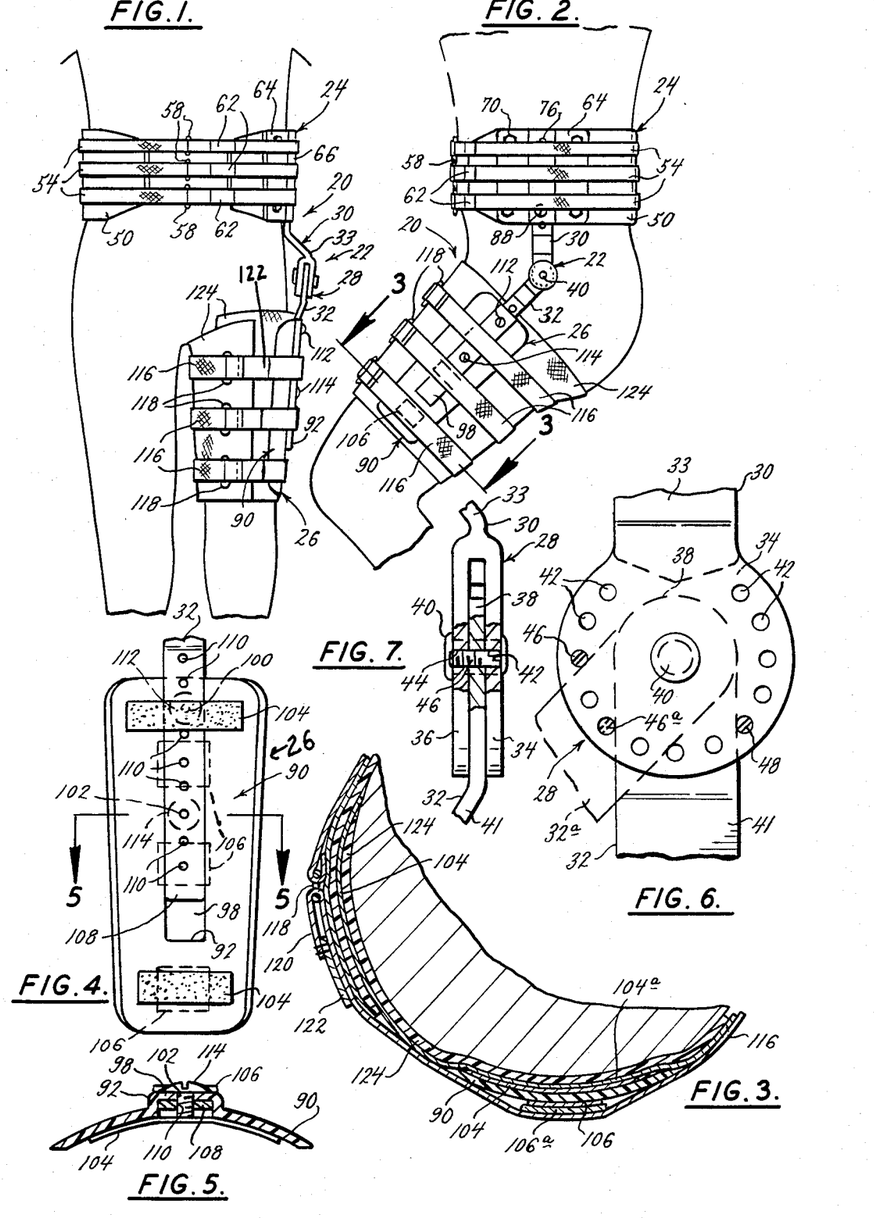
FIG. 1 is a front view of a hip stabilization device using the hinged brace of this invention, shown in use with a patient.
FIG. 2 is a side view of the hinged brace of this invention, used with the stabilizing device on a patient.
FIG. 3 is a partial cross sectional view, taken along line 3—3 in FIG. 2, showing part of the means used to secure the hinge brace to the thigh.
FIG. 4 is an inside, side view of the thigh engaging means of the device showing the adjustable hinge brace mounted thereto.
FIG. 5 is a cross sectional view, taken along line 5—5 of FIG. 4.
FIG. 6 is an exterior side view of the adjustable hinge.
FIG. 7 is a front view of the adjustable hinge taken from the left of FIG. 6.

For purposes of illustration, the hinge brace of this invention shall be illustrated as used with a universal hip stabilization device 20 which is shown as it would be worn by a patient in FIGS. 1 and 2. The stabilization device comprises the adjustable hinged brace 22 of this invention, a first or upper engaging means which in this illustration is a waist engaging means 24, and a second or lower engaging means which in this illustration is a thigh engaging means 26, adjustably engaging the top and the bottom of hinged brace 22, respectively, thereby holding the hinged brace 22 in alignment with the hip joint.

Brace 22 has a hinge 28 and comprises an upper extension member 30 and a lower extension member 32. The lower portion of upper extension 38 is offset at 33 and thence bends downwardly to terminate into a pair of parallel circular plates 34 and 36. Rounded top 38 of lower extension 32 is pivotally engaged between plates 34 and 36 as by a hinge pin 40. The top 38 is offset from the lower part of extension 32 by an angled section 41, so that with offset section 33 of the upper extension 30, the entire hinge 28 is positioned outwardly away from the body, in this case the hip, so as to not rub thereagainst. Plates 34 and 36 have a plurality of aligned holes 42 and 44, respectively, about their circumferences. Holes 44 in plate 36 are threaded, with one such hole being shown in FIG. 7. The range of rotation of lower extension 32 with respect to upper extension 30 can be selectively controlled by the placement of screws 46 and 48 through selected holes 42 and threaded into the corresponding hole 44, as is shown for one pair of holes 42 and 44 in FIG. 7.

Waist engaging means 24 comprises a flexible belt 50, which can be of leather, having an interior side lined with foam padding 52, which can be of synthetic plastic. Belt 50 is fastened to the patient with three straps 54 which encircle belt 50. Velcro TM latching material sewn to the inside of each strap 54 engages respective Velcro TM patches 56 affixed to the exterior of belt 50 as by adhesive, so that straps 54 are secured to belt 50 at the point of the Velcro TM patches 56. One end of each strap 54 is looped at 57 and is sewn to itself with a ring 58 extending through the loop 57. The other strap end 60 has a tab 62 of Velcro TM latching material sewn thereto with the latching material facing outwardly. To secure each strap 54, the end 60 is passed through ring 58, and folded back against strap 54 to be secured thereto by the Velcro TM tab 62 engaging receptive Velcro TM sewn to the outside of strap 54, with such receptive Velcro TM extending a sufficient distance inwardly from the end 60 to allow for sufficient range in tightening each strap.

Figures 8, 9, 10, 11, 12:
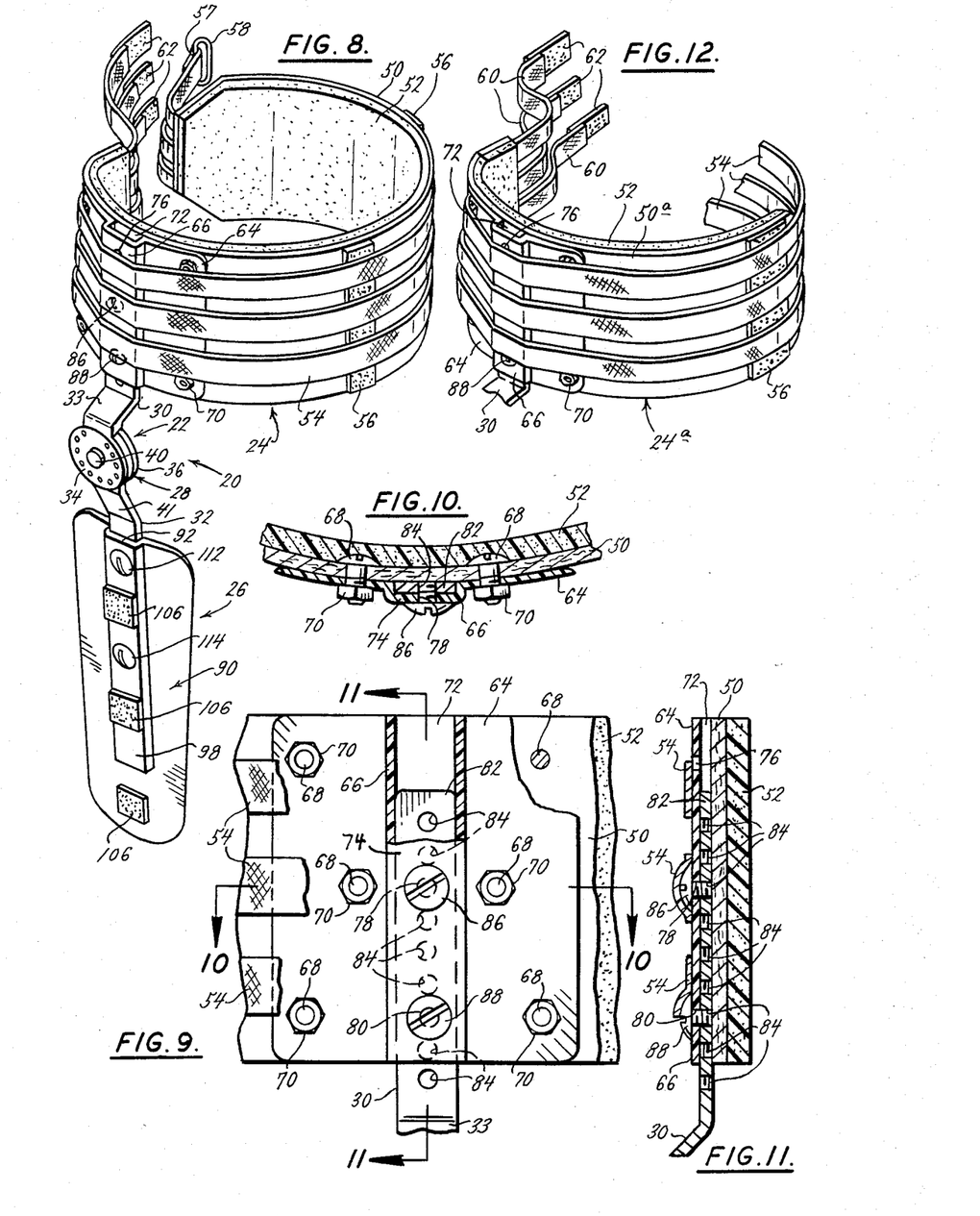
FIG. 8 is an orthogonal projection of the hip device showing the hinge.
FIG. 9 is a partial side view of the waist engaging means of the device showing the engagement of the top of the hinge, with some parts broken.
FIG. 10 is a cross sectional view, taken along line 10—10 in FIG. 9.
FIG. 11 is a cross sectional view, taken along line 11—11 in FIG. 9.
FIG. 12 is an orthogonal projection of a modification of the waist engaging means.

A modification of waist engaging means 24 is shown in FIG. 12. There the belt 50a is shorter. In this form the belt is more adaptable to patients with smaller waists. The fastening of the belt 50a is the same as described for belt 50, with the other parts otherwise being the same.

The adjustable engagement between brace 22 and waist engaging means 24 is shown in enlarged detail views in FIGS. 9, 10 and 11. The waist engaging means 24 further comprises a plate 64, which can be of rigid plastic or of metal, having a unitary rectangular channel 66 formed approximately in its middle, is attached to the exterior of belt 50 by nuts 70 and bolts 68 extending through the belt 50 so that channel 66 and belt 50 define a vertical rectangular sheath 72. The outwardly facing wall 74 of channel 66 has three equally spaced threaded holes 76, 78 and 80 for receiving screws to be described. Upper brace extension 30 has in its top portion 82 a plurality of equally spaced threaded holes 84, which are spaced so that as the upper extension 30 is moved telescopically within sheath 72, the holes 84 can be positioned to be aligned with the lower two channel holes 78 and 80. Two screws 86 and 88 are threaded through holes 78 and 80 of channel 66 and threaded through the aligned holes 84 of upper extension 30 to firmly mount brace upper extension 30 within sheath 66 and thereby mount brace 22 to belt 50.

Belt 50 can be turned over so that sheath 72 is positioned on the other side of the patient, which allows the one belt to engage the brace to support either hip joint. Upper extension 30 is telescopically received in sheath 72 on the other side of the patient, and is positioned so that holes 84 are aligned with the lower two holes in channel 66, now 76 and 78 because of the turning of belt 50. The two screws 86 and 88 are threaded into holes 76 and 78 of channel 66 and through the selected aligned threaded holes 84 of upper extension 30 to securely mount upper extension 30 within sheath 66 and thereby firmly mount brace 22 to belt 50.

Referring now more to FIGS. 2-5, and 8, thigh engaging means 26 comprises an arcuate shaped plastic support 90 which is shaped to conform to the natural curvature of the thigh. Support 90 has a unitary rectangular channel 92 formed approximately in its middle. The outwardly facing wall 98 of channel 92 is provided with two threaded holes 100 and 102 for receiving screws to be described. The inside of support 90 is provided with two patches 104 of Velcro TM latching material, secured thereto as by adhesive. The outside of support 90 is provided with three equally spaced patches 106 of Velcro TM latching material, secured thereto as by adhesive.

Lower brace extension 32 has in its bottom portion 108 a plurality of equally spaced threaded holes 110, which are spaced so that as the lower extension 32 is moved telescopically within channel 92, the holes 110 can be positioned to be aligned with holes 100 and 102 in channel 92. Two screws 112 and 114 are threaded into holes 100 and 102 of channel 92 and through the selected aligned threaded holes 110 of lower extension 32 to securely mount the lower extension 32 within channel 92 and thereby firmly mount the hinged brace 22 to support 90. A backing plate (not shown) can be mounted on the inside of support 90, and secured thereto as by adhesive. The backing plate would thus define a vertical, rectangular sheath between the backing plate and support 90, to achieve a secure engagement between hinged brace 22 and support 90.

Support 90 is fastened to the patient's thigh with three straps 116 which encircle support 90. The inside of each strap 116 is provided with a patch of Velcro TM latching material 106a (FIG. 3) sewn to the inside of each strap 116 to engage the receptive Velcro TM patches 106 on the outside of support 90 to detachably secure the straps to support 90. One end of each strap 116 is looped as described for straps 54 to secure a ring 118. The other strap 116 end 120 has a tab 122 of Velcro TM latching material sewn thereto facing outwardly. To secure each strap 116, the end 120 passes through the ring 118, and is folded back against strap 116 to be secured thereto by the Velcro TM tab 122 which engages receptive Velcro TM (not shown) latching material sewn to the exterior of strap 116.

A separate protective synthetic plastic foam pad 124 can be interposed between the patient's thigh, and the support 90 and straps 116, by wrapping pad 124 around the patient's thigh. The exterior of pad 124 is lined with a layer 104a of Velcro TM latching material, with lining 104a engaging the receptive Velcro TM patches 104 to detachably secure pad 124 to support 90. Alternatively, permanent foam padding can be provided on the inside side of support 90.

OPERATION

In operation, the hinged brace, as illustrated with the hip stabilization device, can be used on either side of the hip. For purposes of illustration, we assume that the left side of the hip area is injured, so that the stabilization device and hinged brace are applied by the operator to the left hip such as shown in FIGS. 1 and 2. For initial application, the belt 50, the brace 22, and the support 90 can all be detached from each other. Upon selection of the left side of the hip, the belt 50 is extended about the patient's waist so that the sheath 72 is aligned to extend downwardly towards the left hip joint. The belt 50 is then secured in place by the three straps 54 with each of the strap ends 60 extending through their corresponding rings 58 and folded back so that the Velcro ™ tabs 62 latch with their corresponding Velcro ™ latching material to give the straps 54 and the belt 50 a snug but comfortable fit.

The brace 22 can then be mounted to the sheath 72 and belt 50. When first applied, the limit screw 48 can be installed while the limit screw 46 can be removed so that the hinge 28 can pivot towards flexing the knee for ease of application. The operator takes the brace 22 and slides the upper brace extension 82 into the sheath 72 until two of the holes 84 in the upper brace portion 82 are aligned with holes 78 and 80 in channel side 74 at a point where the hinge 22 is aligned with the hip joint. The screws 78 and 80 can then be passed through the said holes as previously described to secure the upper brace extension 30 to the sheath 72 and belt 50.

Next, the thigh engaging means 26 can be secured about the thigh and to the brace 22. If it is desired to have the pad 124 applied to the patient's thigh, it is first wrapped around the thigh such as shown in FIG. 1.

The support 90 is then grasped by the operator's hand and moved upwardly from the knee towards the hip so that the lower brace extension 32 is slid into the channel 92 until holes 110 in lower brace extension 32, are in alignment with the holes 100 and 102 in the channel wall for the proper positioning of the support 90 against the thigh. Once the position for the support 90 is selected, screws 112 and 114 are inserted through the holes 100 and 102 and screwed therein as well as into the corresponding holes 110 in the brace extension 32 to secure extension 32 to the support as described previously.

The straps 116 are then passed around the support 90 so that the Velcro ™ on the inside of each of the straps 116 is aligned with each of the Velcro ™ patches 106 on the exterior of the support 90, and the ends of the straps 116 are secured by passing the strap ends 120 through the corresponding rings 118 and looping the ends 120 back to latch against the straps 116 as described previously.

Initially, during the time period immediately following the injury, it may be desired to limit hip movement. The device 20 can be thus fitted so that the brace extensions 30 and 32 extend in alignment with one another such as shown in FIG. 8, and as shown in solid lines in FIG. 6. To lock the brace extensions 30 and 32 in this position screw 48 is positioned as shown in FIG. 6 while screw 46 would be moved downard two of the holes 42 to be placed as shown as 46a. As the patient heals and flexion movement is allowed, the screw can be moved clockwise from position 46a to the next hole and eventually clockwise again to be positioned as shown in FIG. 6. Such positioning allows the lower brace extension 32 to move from the position shown in solid lines in FIG. 6 to the position shown in dashed lines in FIG. 6 as 32a. More flexion can be allowed by moving screw 46 farther clockwise from its FIG. 6 position. The degree of extension can of course likewise be adjusted by moving screw 48 to be inserted in another selected hole 42.

The device 20 thus mounted as shown in FIGS. 1 and 2 prevents rotation of the hip joint, as in the crossing of the leg. Abduction, the sideways movement of the leg, is also prevented. Only flexion, the raising of the leg, and extension, the lowering of the leg, is permitted. The range of flexion and extension is completely adjustable to permit the maximum flexion and extension consistent with the patient's injuries. As the healing progresses, the range of flexion motion can be increased by more clockwise (FIG. 6) movement of the screw 46 in the holes such as previously described so that the muscles, tendons and joints do not atrophy during the healing process.

The device can be quickly detached by removing the straps 54 from engagement with the rings 58 about the belt 50, and removal of the straps 116 from the locking rings 118. The screws 112 and 114 can be removed from engagement with lower extension 32 and support 90 can then be slid downwardly away from lower brace extension 32 to remove extension 32 from channel 92 and disengage support 90 from the brace 22. Likewise the screws 86 and 88 can be removed from sheath 72 and the upper brace extension 30 slid downwardly out of sheath 72 to disengage the brace 22 therefrom.

The use of the smaller waist engaging means shown as 24a in FIG. 12 with the shorter belt 50a is the same as described heretofore for belt 50.

The components thus can be separately stored or can be stored together in disassembled form to take up much less space than in the connected form. The device can be reused on a patient with an injury associated with the right hip by simply flipping the belt over so that the sheath 72 is positioned on the right side of the patient and so that the hole 76 is now the lower of the three holes 76, 78 and 80 in the channel wall 74. The sheath 72 is then aligned with the right hip in the same fashion as described for the left hip, and the hinge 28, and the support 90 and pad 124 are also aligned and attached as described previously.

However although the hinge limit screws 46 and 48 likewise are positioned on the right hip to first resist flexion, the movement of the screws 46 and 48 are the reverse of that described for the left side, with the screw 46 remaining in position 46a as shown looking at the exterior of the hinge in FIG. 6, and with the screw 48 being moved counterclockwise about the hinge 28 in the holes 42 and 44 to permit a greater range of flexion.

The belt straps 54, are detachable from the belt 50, its padding 54 and mounting plate 64, and the belt 50 is likewise detachable from the brace 32. The brace 32 is in turn detachable from the thigh support 90, and the straps 118 and pad 124 are detachable from one another and from support 90. This interchangability of the hinged brace from the various components is advantageous in that should one of the components become damaged and need replacement, it is necessary to replace only that component rather than to bring the entire unit in for repair. This facilitates maintenance and enhances the ease of operability. Thus only the single component need be shipped to the manufacturer for repair. The detachability of the hinged brace from the other components also brings about the universal applicability of the device to the right or left hip.

The detachability of the hinged brace from the various components further enhances storage in that, if desired, the entire unit can be disassembled and all the components stored in one compartmentalized area. On the other hand, detachability of components allows multiple units of the devices to be stored with the hinged braces stored in one compartment, the thigh supports stored in another compartment, and so on. Thus, greater stock can be maintained of components which show a tendency to wear out sooner than the other components.

The hinged brace 22 can be used with other human body joints such as the ankle, knee or elbow for example, in combination with supporting structure affixed or wrapped around the surrounding body area on the sides of the joint. With use with the ankle, knee or elbow, the screws can likewise be inserted in the desired holes in the upper brace extension to permit the desired range of flexion and extension for the joint depending on the nature of the injury, or the desired limitation of movement. The size of the brace and its parts can be varied according to the part of the body with which the brace is used, and the size of the person. To provide a greater variety of ranges of pivotal movement, the holes about the pivot pin can be made smaller, and the screws if necessary be made of stronger material. A second ring of holes can also be provided interior or anterior to the first ring, and the size of the plates at the end of the upper extension can be increased if needed to provide adequate space for the additional ring of holes.

What is claimed is:

1. An orthopedic limited range hinge brace for stabilizing a human bone joint on the exterior of the human body, in combination with supporting members affixed to the body about the joint, comprising:
   (a) a first brace extension;
   (b) a second brace extension;
   (c) means for pivotally mounting the first brace extension to the second brace extension;
   (d) means for selectively limiting the range of pivoting of the brace extensions relative to each other, said means being adjustable to limit pivoting over different ranges while maintaining pivotal engagement of the extensions to each other, and having means to be adjusted while the brace is mounted in use on the body, comprising at least one limiting member attachable to the first extension at a first location near the inner end of the first extension so that the limiting member blocks the second extension to restrict the second extension from pivoting farther in a first direction when the first and second extensions are at a first relative position to each other, with said limiting member being detachable from the said first location on the first extension and reattachable at a second location on the said first extension so that at said second location it restricts pivoting of the second extension in the first direction when the first and second extensions are at a second relative position to each other that is different from the said first relative position.

2. The structure of claim 1 wherein the first brace extension has a plurality of holes located at different positions about the pivotal connection of the extensions, and the limiting member has means to be passed into and be secured within a selected hole of the first extension to block pivotal movement of the second extension relative to the first extension at a first relative positioning of the two extensions, and to be detached from the said first hole and inserted within a second hole at a different position and secured therein to block pivotal movement of the second extension relative to the first extension at a second relative positioning of the first extension to the second extension that is different from the said first relative positioning.

3. The structure of claim 2 further comprising a second limiting member, with the first and second limiting members capable of being inserted and secured within separate holes of the first extension so that the second extension can pivot relative to the first extension with pivotal movement of the first extension in a first direction being blocked at a selected first relative position of the first and second extensions by the first limiting member, and pivotal movement in a second direction being blocked at a second relative position of the first and second extensions by the second limiting member, with the first and second limiting members being detachable from their said holes with means to be inserted and held within other third and fourth holes respectively so that when the first limiting member is mounted within the third hole it blocks pivotal movement of the second extension relative to the first extension in the first direction at a third relative position of the extensions which is different than the first relative position, and when the second limiting member is mounted in the fourth hole it blocks pivotal movement of the second extension relative to the first extension in the second direction at a fourth relative position of the extensions which is different than the second relative position of the extensions, so that the degree of pivotal range of the second extension to the first extension can be adjusted to cover different arcs of movement.

4. The structure of claim 2 wherein the holes in the first extension are threaded and the limiting member is a screw that can thread into the holes.

5. The structure of claim 3 wherein the holes in the first extension are threaded and both limiting members are screws that can thread into the holes.

6. The structure of claim 2 wherein the limiting member acts to block the movement of the second extension by contacting the second extension.

7. The structure of claim 6 wherein the limiting member contacts a side edge of the second extension.

8. The structure of claim 3 wherein the limiting members act to block the second extension pivotal movement by contacting the second extension.

9. The structure of claim 8 wherein the first and second limiting members contact the second extension on opposite sides of the second extension.

10. An orthopedic limited range hinge brace for stabilizing a human bone joint on the exterior of the human body in combination with supporting members affixed to the body about the joint, comprising:
   (a) a first brace extension;
   (b) a second brace extension;
   (c) means for pivotally mounting the first brace extension to the second brace extension;
   (d) means for selectively limiting the range of pivoting of the brace extensions relative to each other, said means being adjustable to limit pivoting over different ranges while maintaining pivotal engagement of the extensions to each other, and having means to be adjusted while the brace is mounted in use on the body, comprising first and second limiting members attachable at first and second locations on the first extension, but being detachable therefrom to be attached at various locations on the first extension, so that when the first and second limiting members are attached at first and second locations respectively on the first extension, the second extension pivots relative to the first extension in a first direction with the first limiting member blocking further pivotal movement of the second extension in the first direction, and so that when the second extension pivots relative to the first extension in a second direction the second limiting member blocks further pivotal movement of the second extension in the second direction, and when the first and second limiting members are placed at third and fourth locations on the first extension which locations are different from said first and second locations, the first limiting member at the third location blocks pivotal movement of the second extension relative to the first extension in the first direction at a different point than when said first limiting member is at said first location, and the said second limiting member at said fourth location blocks pivotal movement of the second extension relative to the first extension in the second direction at a different point than when said second limiting member is in said second location, to provide for different ranges of arcuate movement of the second extension to the first extension.

11. An orthopedic limited range hinge brace for stabilizing a human bone joint on the exterior of the human body in combination with supporting members affixed to the body on sides of the joints comprising;
   (a) a first brace extension having an inner end with a plurality of holes arranged about the inner end;
   (b) a second brace extension having an inner end;
   (c) means for pivotally mounting the inner end of the first extension to the inner end of the second extension;
   (d) means for selectively and adjustably limiting the range of pivoting of the brace extensions relative to each other, said means capable of adjustment while maintaining pivotal engagement of the extensions to each other while the brace is mounted in use on the body, comprising a first limiting member and a second limiting member mounted in first and second holes respectively of the first extension, but being detachable from said holes by removal outwardly away from the first extension to allow each limiting member to be attached in various of the plurality of holes, so that when the two limiting members are attached within the first and second holes, the second extension pivots relative to the first extension in a first direction with the first limiting member contacting said second extension to block further pivotal movement in the first direction, and so that when the second extension pivots relative to the first extension in a second direction the second limiting member contacts the second extension to block pivotal movement of the second extension in the second direction, and so that when the first and second limiting members are placed within another separate pair of third and fourth holes respectively in the first extension the first limiting member in the third hole contacts the second extension to block pivotal movement of the second extension relative to the first extension in the first direction at a different point than when said first limiting member is in said first hole, and the said second limiting member in said fourth hole contacts the second extension to block pivotal movement of the second extension relative to the first extension in the second direction at a different point than when said second limiting member is in said second hole, to provide for different ranges of arcuate movement of the second extension relative to the first extension.

12. The structure of claim 11 wherein the limiting members are screws and the holes in the first extension have matching threads.

13. An orthopedic limited range hinge brace stabilizing a human bone joint on the exterior of the human body in combination with supporting members affixed to the body on sides of the joint comprising;
   (a) a first brace extension having an inner end terminating in two places, the said plates each having a plurality of aligned holes;
   (b) a second extension having an inner end;
   (c) a pin pivotally mounting the inner end of the first extension to the inner end of the second extension;
   (d) means for adjustably limiting the range of pivoting of the second extension relative to the first extension comprising a first limiting member for placement within a selected first pair of aligned holes of each of the plates so that said limiting member contacts the second extension when it is pivoted in a first direction relative to the first extension to block further movement of the second extension in the first direction when the extensions are in a first relative position to each other, with the limiting member having means to be detached from the first pair of aligned holes and inserted within a second pair of aligned holes to block pivoting of the second extension in the first direction when the extensions are in a second relative position to each other that is different from the said first relative position.

14. The structure of claim 13 wherein the means for limiting pivotal movement further comprises a second limiting member for placement in a second pair of aligned holes in the plates, to contact the second extension when it is pivoted in a second direction to block further movement in the second direction, with both the first and second limiting members being detachable from their respective holes by being moved outwardly away from the plates and reattachable to be secured within other different third and fourth pairs of holes in the aligned plates to block movement of the second extension in both the first and second pivotal directions at different points of relative positioning of the first extension to the second extension than the points of blocking when the limiting members are in the first and second pair of holes, so that the range of pivotal movement of the second extension relative to the first extension in the said first and second directions can be adjusted to provide different positions of blocking of the second extension to the first extension and different ranges of arcuate movement of the second extension to the first extension.

15. The structure of claim 14 wherein the holes of the second extension are threaded and the limiting members are screws with matching threads.

16. An orthopedic limited range hinge brace for stabilizing a human bone joint on the exterior of the human body, in combination with supporting members affixed to the body about the joint, comprising:
   (a) a first brace extension;
   (b) a second brace extension;
   (c) means for pivotally mounting the first brace extension to the second brace extension;
   (d) means for selectively limiting the range of pivoting of the brace extensions relative to each other, said means capable of adjustment to limit pivoting over different ranges while maintaining pivotal engagement of the extensions to each other, and having means to be adjusted while the brace is mounted in use on the body, comprising a first limiting member attachable to one of the extensions at a first location, and a second limiting member attachable to one of the extensions at a second location, so that when the second extension pivots relative to the first extension in a first direction, the first limiting member acts to block further pivotal movement in the first direction at a first relative position of the extensions, and so that when the second extension pivots relative to the first extension in a second direction, the second limiting member acts to block pivotal movement of the second extension in the second direction at a second relative position of the extensions, so that pivoting is limited to a pre-determined arc between the two limiting members, with said limiting members each being detachable from the location on the extension to which it is attached and having means to be reattached at a third location on an extension and a fourth location on an extension so that at said third location the first limiting member blocks pivotal movement of the second extension relative to the first extension at a third relative position of the two extensions different from the said first relative position of the two extensions, and the second limiting member at the fourth location acts to block pivotal movement of the second extension relative to the first extension at a different relative position of the extensions than the said second relative position of the extensions.

17. The structure of claim 16 wherein the first and second limiting members are attached to the same extension.

18. An orthopedic limited range hinge brace for stabilizing a human bone joint on the exterior of the human body, in combination with supporting members affixed to the body about the joint, comprising:
(a) a first brace extension;
(b) a second brace extension;
(c) means for pivotally mounting the first brace extension to the second brace extension, the portion of the second brace extension near the pivotal connection to the first extension having a substantially symmetrical shape along its longitudinal axis, with the pivotal connection of the second brace extension being at a point approximately on the longitudinal axis of the second extension;
(d) means for selectively limiting the range of pivoting of the brace extensions relative to each other, said means being adjustable to limit pivoting over different ranges while maintaining pivotal engagement of the extensions to each other, and having means to be adjusted while the brace is mounted in use on the body, comprising at least one limiting member attachable to the first extension at a first location near the inner end of the first extension so that the limiting member engages the second extension to restrict the second extension from pivoting farther in a first direction when the first and second extensions are at a first relative position to each other, with said limiting member being detachable from the said first location on the first extension and reattachable at a second location on the said first extension so that at said second location it engages the second extension to restrict pivoting of the second extension in the first direction when the first and second extensions are at a second relative position to each other that is different from the said first relative position.

19. The structure of claim 18 wherein the first brace extension has a longitudinal axis and the pivotal connection to the second extension is at a point approximately on the longitudinal axis of the first extension.

20. An orthopedic limited range hinge brace for stabilizing a human bone joint on the exterior of the human body in combination with supporting members affixed to the body about the joint, comprising:
(a) a first brace extension;
(b) a second brace extension having at least two substantially parallel sides, the first side being on substantially the opposite side of the second side;
(c) means for pivotally mounting the first brace extension to the second brace extension;
(d) means for selectively limiting the range of pivoting of the brace extensions relative to each other, said means being adjustable to limit pivoting over different ranges while maintaining pivotal engagement of the extensions to each other, and having means to be adjusted while the brace is mounted in use on the body, comprising first and second limiting members attachable at first and second locations on the first extension, but being detachable therefrom to be attached at various locations on the first extension, so that when the first and second limiting members are attached at first and second locations respectively on the first extension, the second extension pivots relative to the first extension in a first direction with the first limiting member engaging the first side of the second extension to block further pivotal movement of the second extension in the first direction, and so that when the second extension pivots relative to the first extension in a second direction the second limiting member engages the second side of the second extension to block further pivotal movement of the second extension in the second direction, and when the first and second limiting members are placed at third and fourth locations on the first extension which locations are different from said first and second locations, the first limiting member at the third location engages the first side of the second extension to block pivotal movement of the second extension relative to the first extension in the first direction at a different point than when said first limiting member is at said first location, and the said second limiting member at said fourth location engages the second side of second extension to block pivotal movement of the second extension relative to the first extension in the second direction at a different point than when said second limiting member is in said second location, to provide for different ranges of arcuate movement of the second extension to the first extension.

21. An orthopedic limited range hinge brace for stabilizing a human bone joint on the exterior of the human body in combination with supporting members affixed to the body on sides of the joints comprising:
(a) a first brace extension having a substantially symmetrical shape along its longitudinal axis, and having an inner end with a plurality of holes arranged about the inner end;
(b) a second brace extension having a substantially symmetrical shape along its longitudinal axis and having an inner end and having first and second substantially parallel sides;
(c) means for pivotally mounting the inner end of the first extension to the inner end of the second extension at a point on the longitudinal axes of the first and second extensions with the plurality of holes extending about the pivotal connection in a substantially circular pattern;

(d) means for selectively and adjustably limiting the range of pivoting of the brace extensions relative to each other, said means capable of adjustment while maintaining pivotal engagement of the extensions to each other while the brace is mounted in use on the body, comprising a first limiting member and a second limiting member mounted in first and second holes respectively of the first extension, but being detachable from said holes by removal outwardly away from the first extension to allow each limiting member to be attached in various of the plurality of holes, so that when the two limiting members are attached within the first and second holes, the second extension pivots relative to the first extension in a first direction with the first limiting member contacting the first side of said second extension to block further pivotal movement in the first direction, and so that when the second extension pivots relative to the first extension in a second direction the second limiting member contacts the second side of the second extension to block pivotal movement of the second extension in the second direction, and so that when the first and second limiting members are placed within another separate pair of third and fourth holes respectively in the first extension the first limiting member in the third hole contacts the first side of the second extension to block pivotal movement of the second extension relative to the first extension in the first direction at a different point than when said first limiting member is in said first hole, and the said second limiting member in said fourth hole contacts the second side of the second extension to block pivotal movement of the second extension relative to the first extension in the second direction at a different point than when said second limiting member is in said second hole, to provide for different ranges of arcuate movement of the second extension relative to the first extension.

22. An orthopedic limited range hinge brace for stabilizing a human bone joint on the exterior of the human body in combination with supporting members affixed to the body about the joint, comprising:

(a) a first brace extension;
(b) a second brace extension having at least two substantially parallel sides, the first side being on substantially the opposite side of the second side;
(c) means for pivotally mounting the first brace extension to the second brace extension, the portion of the second brace extension near the pivotal connection to the first extension having a substantially symmetrical shape along its longitudinal axis, with the pivotal connection of the second brace extension being at a point approximately on the longitudinal axis of the second extension;

(d) means for selectively limiting the range of pivoting of the brace extensions relative to each other, said means being adjustable to limit pivoting over different ranges while maintaining pivotal engagement of the extensions to each other, and having means to be adjusted while the brace is mounted in use on the body, comprising first and second limiting members attachable at first and second locations on the first extension, but being detachable therefrom to be attached at various locations on the first extension, so that when the first and second limiting members are attached at first and second locations respectively on the first extension, the second extension pivots relative to the first extension in a first direction with the first limiting member engaging the first side of the second extension to block further pivotal movement of the second extension in the first direction, and so that when the second extension pivots relative to the first extension in a second direction the second limiting member engages the second side of the second extension to block further pivotal movement of the second extension in the second direction, and when the first and second limiting members are placed at third and fourth locations on the first extension which locations are different from said first and second locations, the first limiting member at the third location engages the first side of the second extension to block pivotal movement of the second extension relative to the first extension in the first direction at a different point than when said first limiting member is at said first location, and the said second limiting member at said fourth location engages the second side of the second extension to block pivotal movement of the second extension relative to the first extension in the second direction at a different point than when said second limiting member is in said second location, to provide for different ranges of arcuate movement of the second extension to the first extension.

23. The structure of claim 22 wherein the means for selectively limiting the range of pivoting comprises the first extension having a plurality of holes arranged about the pivotal connection of the extension with the limiting members being securely mounted in selected holes of the first extension; and wherein the first extension has a longitudinal axis with the pivotal connection being approximately on said longitudinal axis.

* * * * *